(12) United States Patent
Saunders et al.

(10) Patent No.: US 11,306,323 B2
(45) Date of Patent: *Apr. 19, 2022

(54) EXPRESSION PROCESS

(71) Applicant: Fujifilm Diosynth Biotechnologies UK Limited, Billingham (GB)

(72) Inventors: Fay Louise Saunders, Billingham (GB); Anna Louise Dodds, Billingham (GB); Adeline Marie Geraldine Bayard, Billingham (GB); Bhupendra Vallabh Kara, Billingham (GB)

(73) Assignee: Fujifilm Diosynth Biotechnologies UK Limited, Billingham (GB)

( * ) Notice: Subject to any disclaimer, the term of this patent is extended or adjusted under 35 U.S.C. 154(b) by 885 days.

This patent is subject to a terminal disclaimer.

(21) Appl. No.: 15/838,868

(22) Filed: Dec. 12, 2017

(65) Prior Publication Data

US 2018/0127777 A1 May 10, 2018

Related U.S. Application Data

(63) Continuation of application No. 14/787,669, filed as application No. PCT/GB2014/000165 on Apr. 29, 2014, now Pat. No. 9,873,891.

(30) Foreign Application Priority Data

May 3, 2013 (GB) ..................................... 1308017
Nov. 18, 2013 (GB) ..................................... 1320339

(51) Int. Cl.
*C12N 15/85* (2006.01)
*C07K 16/06* (2006.01)
*C07K 16/30* (2006.01)

(52) U.S. Cl.
CPC ............ *C12N 15/85* (2013.01); *C07K 16/065* (2013.01); *C07K 16/3092* (2013.01); *C07K 2317/14* (2013.01); *C07K 2319/02* (2013.01)

(58) Field of Classification Search
CPC combination set(s) only.
See application file for complete search history.

(56) References Cited

U.S. PATENT DOCUMENTS

2003/0228284 A1   12/2003   McCown et al.
2012/0027769 A1   2/2012    Daftary et al.

FOREIGN PATENT DOCUMENTS

| KR | 10-2010-0027352 A | 3/2010 |
| WO | 03/093295 A2 | 11/2003 |
| WO | 2010/102251 A2 | 9/2010 |

OTHER PUBLICATIONS

International Search Report and Written Opinion issued in corresponding International Patent Application No. PCT/GB2014/000165 dated Jul. 21, 2014.

*Primary Examiner* — James D Schultz
(74) *Attorney, Agent, or Firm* — Morgan, Lewis & Bockius LLP

(57) ABSTRACT

A process for the production of a target polypeptide is provided. The process comprises expression of an expression vector for expressing a target polypeptide in a host cell, preferably a mammalian cell, the expression vector comprising an expression cassette comprising a polynucleotide encoding a recombinant polypeptide operably linked to a fibronectin secretion leader sequence; and recovering the target polypeptide.

10 Claims, 1 Drawing Sheet
Specification includes a Sequence Listing.

Structure of Expression Cassettes
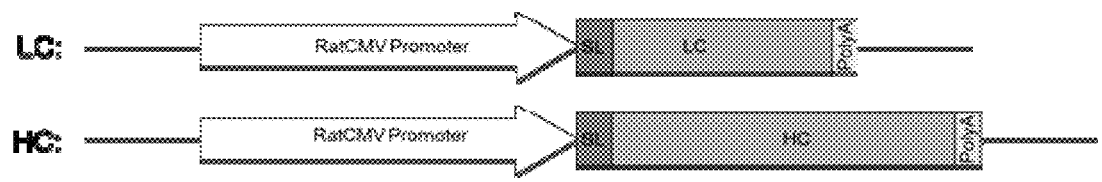

SEQUENCE LISTING

<160> NUMBER OF SEQ ID NOS: 6

<210> SEQ ID NO 1

```
<211> LENGTH: 26
<212> TYPE: PRT
<213> ORGANISM: Homo sapiens

<400> SEQUENCE: 1

Met Leu Arg Gly Pro Gly Pro Gly Leu Leu Leu Ala Val Gln Cys
1               5                   10                  15

Leu Gly Thr Ala Val Pro Ser Thr Gly Ala
            20                  25

<210> SEQ ID NO 2
<211> LENGTH: 25
<212> TYPE: PRT
<213> ORGANISM: Cricetulus griseus

<400> SEQUENCE: 2

Met Leu Arg Gly Pro Gly Pro Gly Leu Leu Leu Ala Val Leu Cys Leu
1               5                   10                  15

Gly Thr Ala Val Arg Cys Thr Glu Ala
            20                  25

<210> SEQ ID NO 3
<211> LENGTH: 78
<212> TYPE: DNA
<213> ORGANISM: Homo sapiens

<400> SEQUENCE: 3
atgctgagag gccctggacc tggactgctg ctgctggctg tgcagtgtct gggaaccgcc     60
gtgccttcta ccggcgcc                                                  78

<210> SEQ ID NO 4
<211> LENGTH: 75
<212> TYPE: DNA
<213> ORGANISM: Cricetulus griseus

<400> SEQUENCE: 4
atgctcaggg gtccgggacc cgggctgctg ctggccgtcc tgtgcctggg gacagcggtg     60
cgctgtaccg aagcc                                                     75

<210> SEQ ID NO 5
<211> LENGTH: 24
<212> TYPE: PRT
<213> ORGANISM: Homo sapiens

<400> SEQUENCE: 5

Met Leu Ser Phe Val Asp Thr Arg Thr Leu Leu Leu Ala Val Thr
1               5                   10                  15

Leu Cys Leu Ala Thr Cys Gln Ser
            20

<210> SEQ ID NO 6
<211> LENGTH: 18
<212> TYPE: PRT
<213> ORGANISM: Cricetulus griseus

<400> SEQUENCE: 6

Met Lys Trp Val Thr Phe Leu Leu Leu Leu Phe Val Ser Asp Ser Ala
1               5                   10                  15

Phe Ser
```

EXPRESSION PROCESS

SEQUENCE LISTING SUBMISSION VIA EFS-WEB

A computer readable text file, entitled "SequenceListing.txt" created on or about Dec. 11, 2017, with a file size of about 2 kb contains the sequence listing for this application and is hereby incorporated by reference in its entirety.

The present invention concerns a process for the expression of recombinant polypeptides, and in particular the secretion of recombinant polypeptides.

It is of significant benefit in recombinant polypeptide production if the polypeptide of interest can be exported from the cell in which it is expressed. Expression systems are therefore advantageously designed to enable such export, or secretion. Secretion of the recombinant polypeptide from the host cell commonly involves use of signal peptides, which are found on the majority of eukaryotic and prokaryotic proteins that are destined for export from the cytoplasm. Secretion leaders employed in such expression systems are typically native to the expression host, for example, the PhoA, MalB and OmpA signal peptides of *Escherichia coli* have been used extensively to secrete polypeptides to the periplasm of that organism.

U.S. Pat. No. 7,071,172 describes the use of fibronectin secretion leaders in AAV-based delivery vectors for use in gene therapy.

BRIEF DESCRIPTION OF DRAWINGS

FIG. 1 illustrates a structure of an exemplary expression cassette according to Example 1.

According to a first aspect of the present invention, there is provided a process for the production of a target polypeptide which comprises:

a) expressing an expression vector for expressing a target polypeptide in a host cell, the expression vector comprising an expression cassette comprising a polynucleotide encoding a recombinant polypeptide operably linked to a fibronectin secretion leader sequence or a functional equivalent thereof; and b) recovering the target polypeptide.

Fibronectin secretion leaders that can be employed in the present invention include mammalian and reptilian fibronectin secretion leaders. Examples of reptilian fibronectin secretion leaders include *Xenopus laevis* fibronectin secretion leaders. Examples of mammalian fibronectin secretion leaders include human, rat, murine, bovine, porcine, canine, feline and Chinese hamster fibronectin secretion leaders, and functional equivalents thereof, such as human fibronectin secretion leader having the sequence MLRGPGPGLLLLAVQCLGTAVPSTGA (SEQ ID No. 1). In certain embodiments, the Chinese hamster fibronectin secretion leader having the amino acid sequence MLRGPGPGLLLAVLCLGTAVRCTEA (SEQ ID No. 2) and functional equivalents thereof is preferred.

A functional equivalent to a secretion leader is one that shares 70% or greater identity with an amino acid sequence, preferably 75% or greater identity, more preferably 80% or greater identity and most preferably 90% or greater identity, such as 95% identity or more, and which retains the ability to secrete the recombinant polypeptide. In some embodiments, the functionally equivalent secretion leader differs by a single amino acid, by any of addition, deletion or replacement.

In many embodiments, polynucleotide sequences which are operably linked are contiguous and, in the case of a secretion leader, contiguous and in the same reading frame.

Preferably, the linkage between the polynucleotide encoding the fibronectin secretion leader sequence and the polynucleotide encoding the target polypeptide is such that the secretion leader is attached to the N-terminal of the recombinant polypeptide. In certain embodiments, the recombinant polypeptide comprises an N-terminal tag, the linkage between the secretion leader sequence and the polynucleotide encoding the recombinant polypeptide being such that the secretion leader is attached to the tag, preferably to the N-terminus of the tag.

The polynucleotide encoding the fibronectin secretion leader sequence is preferably attached at the 5' end of the polynucleotide encoding the target polypeptide and preferably has the sequence ATGCTGAGAGGCCCTGGACCTGGACTGCTGCTGCTGGCTGTGCAGTGTCTGGAACCGCCGTGCCTTCTACCGGCGCC (SEQ ID No. 3) or ATGCTCAGGGGTCCGGGACCCGGGCTGCTGCTGGCCGTCCTGTGCCTGGGGACAGCGGTGCGCTGTACCGAAGCC (SEQ ID No. 4).

The vectors of the present invention comprise a promoter operably linked to the expression cassette for the secretion leader and recombinant polypeptides.

Promoters which may be employed in the vectors according to the present invention are selected according to the host cell in which the expression cassette is to be expressed.

Promoters that can be employed in prokaryotic host cells include phage polymerase-promoters, such as single T7 promoter regions, including those disclosed by Studier and Moffat, J. Mol. Biol. 189:113-130 (1986), incorporated herein by reference, especially a T7 gene 10 promoter region and host polymerase promoters, especially *E coli* polymerase promoters, such as T7A1, T7A2, T7A3, λpL, λpR, lac, lacUV5, trp, tac, trc, phoA and rrnB.

When a T7 RNA-polymerase dependent promoter region is employed, it will be recognised that a source of T7 RNA polymerase is required, which is provided by methods known in the art, and commonly by inserting a λDE3 prophage expressing the required phage polymerase into the host strain to create lysogenic host strains. The T7 RNA polymerase can also be delivered to the cell by infection with a specialised λ transducing phage that carries the gene for the T7 RNA polymerase.

Promoters that can be employed in yeast host cell include gal promoters and AOX promoters, such as AOX1 and AOX2, GAP (glyceraldehyde 3-phosphate dehydrogenase), FLP (formaldehyde dehydrogenase) and GAL1 and GAL10.

Promoters that can be employed in mammalian host cells may be endogenous or exogenous to the host cells. Suitable promoters include viral promoters such as CMV, SV40 promoter, and RSR-LTR. Promoters from housekeeping genes such as hEF1a and murine phosphoglycerate kinase (mPGK) may also be utilised. In some embodiments, preferred promoters are human CMV and rat CMV. The promoters may be the same or different if more than one polypeptide is being expressed (eg MAb HC and LC polypeptides). The promoter may be employed in combination with an enhancer sequence, such as the major immediate early enhancer of a cytomegalovirus, especially human cytomegalovirus.

The expression vector may be integrated into the host cell genome or comprised within an extrachromosomal element such as a plasmid.

The expression vector typically also comprises a selectable marker appropriate to the host cell in which the vector is to be expressed. Selectable markers for use in prokaryotic host cells include antibiotic resistance markers, such as tetracycline or kanamycin resistance markers. Selectable markers for use in yeast hosts include antibiotic resistance markers, such as Zeocin, puromycin, neocin and hygromycin resistance. Selectable markers for mammalian cells, and especially for Chinese hamster ovary cells include glutamine synthetase and dihydrofolate reductase marker systems.

The vectors employed comprise features conventional in the art appropriate for expression in the appropriate host cell. Prokaryotic expression vectors typically comprise an origin of replication, restriction enzyme sites, a transcription terminator, and a plasmid stability locus, such as a cer stability sequence. Yeast expression vectors typically comprise promoter, transcription terminator, selection marker, and if replicating, an origin of replication. Mammalian expression vectors typically comprise a polyadenylation sequence, such as human betaglobin polyA sequence, bovine growth hormone polyA sequence and SV40 early or late poly A sequences.

The expression vector of the present invention can be employed to express recombinant polypeptides, especially proteins in host cells. Prokaryote and especially eukaryote host cells can be employed. Examples of prokaryotic cells include bacterial cells, for example gram-negative bacterial cells, including *E. coli, Salmonella typhimurium, Serratia marsescens, Pseudomonas putida* and *Pseudomonas aeruginosa*, and gram-positive bacterial cells including *Bacillus subtilis*. Preferred prokaryote host cells are bacteria, particularly enterobacteriacae, preferably *E coli*, and especially B or K12 strains thereof.

Examples of eukaryote host cells which can be employed include yeast, mammalian and insect cells. Yeast host cells include in particular *Saccharomyces cerevisiae, Pichia pastoris* and *Hansenula* polymorphs.

Preferred host cells are mammalian cells, such as baby hamster kidney cells, human embryonic kidney cell lines, for example HEK 293 cells, human retina-derived cell lines, for example PER.C6 cells, and murine lymphoid cell lines, for example NSO and SP2 cells. and most preferably Chinese hamster ovary cells, and in particular CHOK1, DG44, DUXKB11 and CHO pro3-cells.

The expression vector of the present invention is commonly employed in the form of a plasmid. The plasmids may be autonomously replicating plasmids or integrative plasmids.

In certain highly preferred embodiments of the present invention, the fibronectin secretion leader is selected to correspond to the host cell employed. For example, human fibronectin is employed in human-derived cells, rat fibronectin is employed in rat cells, and particularly Chinese hamster fibronectin is employed in Chinese hamster ovary cells.

Polypeptides which can be expressed by the process of the present invention include therapeutic proteins and peptides, including cytokines, growth factors, antibodies, antibody fragments, immunoglobulin like polypeptides, enzyme, vaccines, peptide hormones, chemokines, receptors, receptor fragments, kinases, phosphatases, isomerases, hydrolyases, transcription factors and fusion polypeptides.

Antibodies which can be expressed include monoclonal antibodies, polyclonal antibodies and antibody fragments having biological activity, including multivalent and/or multispecific forms of any of the foregoing.

Naturally occurring antibodies typically comprise four polypeptide chains, two identical heavy (H) chains and two identical light (L) chains inter-connected by disulfide bonds. Each heavy chain comprises a variable region ($V_H$) and a constant region ($C_H$), the $C_H$ region comprising in its native form three domains, $C_H1$, $C_H2$ and $C_H3$. Each light chain comprises a variable region ($V_L$) and a constant region comprising one domain, $C_L$.

The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4.

Antibody fragments which can be expressed comprise a portion of an intact antibody, said portion having a desired biological activity. Antibody fragments generally include at least one antigen binding site. Examples of antibody fragments include: (i) Fab fragments having $V_L$, $C_L$, $V_H$ and $C_H1$ domains; (ii) Fab derivatives, such as a Fab' fragment having one or more cysteine residues at the C-terminus of the $C_H1$ domain, that can form bivalent fragments by disulfide bridging between two Fab derivatives; (iii) Fd fragment having $V_H$ and $C_H1$ domains; (iv) Fd derivatives, such as Fd derivatives having one or more cysteine residues at the C-terminus of the $C_H1$ domain; (v) Fv fragments having the $V_L$ and $V_H$ domains of a single arm of an antibody; (vi) single chain antibody molecules such as single chain Fv (scFv) antibodies in which the $V_L$ and $V_H$ domains are covalently linked; (vii) $V_H$ or $V_L$ domain polypeptide without constant region domains linked to another variable domain (a $V_H$ or $V_L$ domain polypeptide) that is with or without constant region domains, (e.g., $V_H$-$V_H$, $V_H$-$V_L$, or $V_L$-$V_L$) (viii) domain antibody fragments, such as fragments consisting of a $V_H$ domain, or a $V_L$ domain, and antigen-binding fragments of either $V_H$ or $V_L$ domains, such as isolated CDR regions; (ix) so-called "diabodies" comprising two antigen binding sites, for example a heavy chain variable domain ($V_H$) connected to a light chain variable domain ($V_L$), in the same polypeptide chain; and (x) so-called linear antibodies comprising a pair of tandem Fd segments which, together with complementary light chain polypeptides, form a pair of antigen binding regions.

Preferred antibody fragments that can be prepared are mammalian single variable domain antibodies, being an antibody fragment comprising a folded polypeptide domain which comprises sequences characteristic of immunoglobulin variable domains and which specifically binds an antigen (i.e., dissociation constant of 500 nM or less, such as 400 nM or less, preferably 250 nM or less, and most preferably 100 nM or less), and which binds antigen as a single variable domain; that is, without any complementary variable domain. Single variable domain antibodies include complete antibody variable domains as well as modified variable domains, for example in which one or more loops have been replaced by sequences which are not characteristic of antibody variable domains or antibody variable domains which have been truncated or comprise N- or C-terminal extensions, as well as folded fragments of variable domains. Preferred single variable domains which can be prepared are selected from the group of $V_H$ and $V_L$, including $V_{kappa}$ and $V_{lambda}$. Most preferably the single variable domains are human or camelid domains, including humanised camelid domains.

Where the target polypeptide comprises two or more chains to be secreted, particularly where the target polypeptide is an antibody or a fragment antibody comprising two or more chains, at least one, and preferably each, of the chains is attached to a fibronectin secretion leader, and polynucleotides encoding such polypeptides are designed accordingly. The fibronectin secretion leaders employed may be the same or different. The polynucleotides encoding the two or more chains may be comprised within the same expression cassette, but are preferably comprised in different expression cassettes. Where different expression cassettes are employed, the expression cassettes may be located on different vectors, but are preferably on the same vector. Promoters employed may be the same or different.

The expression system is expressed by methods well known in the art for the cells employed. Preferred expression methods include culturing the host cells in growth medium, and then recovering the expressed polypeptide. The term "growth medium" refers to a nutrient medium used for growing the host cells. In many embodiments, a nutrient solution is employed. Suitable growth media for given host cells and methods of recovering polypeptides are well known in the art.

In many embodiments, the polypeptide recovery comprises one or more of filtration, centrifugation, diafiltration, ion-exchange chromatography, affinity chromatography, such as Protein A affinity chromatography, Hydrophobic Interaction Chromatography (HIC), Gel Filtration and HPLC.

According to a preferred aspect of the present invention there is provided a process for the production of a target polypeptide which comprises:

(a) transfection or transformation of a host cell with an expression vector for expressing a target polypeptide in a host cell, the expression vector comprising an expression cassette comprising a polynucleotide encoding the target polypeptide operably linked to a fibronectin secretion leader sequence or a functional equivalent thereof;

(b) culturing the host cell under conditions which allow proliferation of the host cell and expression and secretion of the target polypeptide from the host cell (c) and recovering the target polypeptide.

According to a further aspect of the present invention, there is provided a Chinese hamster ovary cell, preferably a CHOK1, DG44, DUXKB11 or CHO pro3-cell, transfected with an expression vector comprising an expression cassette comprising a polynucleotide encoding the target polypeptide operably linked to a fibronectin secretion leader sequence or a functional equivalent thereof.

The target polypeptide encoded in the further aspect of the present invention is preferably comprises a monoclonal antibody. An expression cassette comprising polynucleotides encoding both heavy and light chains of a monoclonal antibody, preferably each operably linked to a fibronectin secretion leader, may be employed. In some embodiments, separate expression cassettes comprising heavy and light chains are employed, which may be located on separate vectors, but are often located on the same vector. The fibronectin secretion leaders employed may be the same or different, but are preferably the same.

In many preferred embodiments, the expression cassette comprises a housekeeping gene promoter, especially an hEF1a promoter operably linked to the polynucleotide encoding the target polypeptide, and when two or more expression cassettes are employed, each expression cassette comprises a housekeeping gene promoter, preferably the same promoter, and most preferably an hEF1a promoter.

The, or each, expression cassette for the target polypeptide preferably comprises a bovine growth hormone polyA sequence.

The expression vector preferably comprises a selection marker, most preferably a dihydrofolate reductase marker system. In certain instances, the dihydrofolate reductase marker system comprises an expression cassette further comprising a murine phosphoglycerate kinase promoter.

A DNA construct comprising an expression cassette comprising a promoter effective in a mammalian cell and a polynucleotide encoding a target polypeptide operably linked to a fibronectin secretion leader sequence forms another aspect of the present invention.

The DNA constructs preferably comprise separate expression cassettes for heavy and light chains of a monoclonal antibody. Most preferably, each expression cassette comprises the same promoter, especially a housekeeping gene promoter, most especially an hEF1a promoter. Particularly preferably, each expression cassette further comprises a bovine growth hormone polyA sequence. The DNA constructs often advantageously comprise a selection marker, most preferably a dihydrofolate reductase marker system. In certain instances, the dihydrofolate reductase marker system comprises an expression cassette further comprising a murine phosphoglycerate kinase promoter.

The present invention is illustrated without limitation by the following examples.

EXAMPLE 1

For each secretion leader (SL) being assessed, two single gene vectors were constructed which contained either the hγ1 FL heavy chain (HC) of an anti-MUC-1 MAb or the lambda light chain (LC) of an anti-MUC-1 MAb. Each expression cassette consisted of a rat CMV promoter, functionally linked to a polynucleotide sequence encoding the secretion leader which was linked in frame to a polynucleotide sequence encoding the HC or LC mature polypeptide and a human betaglobin polyA sequence. The structure of the expression cassettes is illustrated in FIG. 1.

Secretion leaders employed were as follows:

```
Secretion leader A:
human collagen, sequence
                                    (SEQ ID No. 5)
MLSFVDTRTLLLLAVTLCLATCQS Secretion leader B:
human fibronectin, sequence
                                    (SEQ ID No. 1)
MLRGPGPGLLLLAVQCLGTAVPSTGA Secretion leader C:
Chinese hamster fibronectin, sequence
                                    (SEQ ID No. 2)
MLRGPGPGLLLAVLCLGTAVRCTEA Secretion leader D:
Chinese hamster albumin, sequence
                                    (SEQ ID No. 6)
MKWVTFLLLLFVSDSAFS
```

CHO DG44 host cells were counted and seeded onto wells of a 6 well plate at $1.2 \times 10^6$ cells/well in MEM-α medium supplemented with 10% serum, 2 mM Glutamine and 0.45% glucose, and incubated overnight at 36.5° C., 7.5% $CO_2$.

For each transfection 4 μg of the HC and LC single gene vectors (2 μg) were mixed together and diluted in 250 μL serum free MEM-α medium (Life Technologies). A mock transection (PBS only) was also included. For each transfection 12.5 μL Lipofectamine 2000 (Life Technologies) was diluted in 250 μL serum free MEM-α medium and mixed. The mixture was incubated at room temperature (15-25° C.) for 5 minutes. The diluted DNA and Lipofectamine2000™ reagent were combined, mixed and incubated for 20 minutes at room temperature. A further 500 μL MEM-α medium was added to each transfection mix, growth medium was removed from the well and the complex was then added to a well of the 6-well plate containing the cells. After 5 hours the medium was removed and fresh growth medium was added. Cells were incubated for 5 days at 36.5° C., 7.5% $CO_2$. Supernatant was harvested and clarified by centrifugation. Antibody titre was determined using an Octet (Forte Bio) protein A assay.

The results are given in Table 1 below.

TABLE 1

| Secretion leader used | Mean antibody titre (mg/l) |
|---|---|
| A | 2.91 |
| B | 7.79 |
| C | 8.85 |
| D | 1.89 |

The antibody produced is recovered from the supernatant by Protein A capture, elution at low pH and purified by cation exchange chromatography followed by anion exchange chromatography. Eluent from the anion exchange chromatography is subject to viral nanofiltration, followed by buffer exchange and concentration.

EXAMPLE 2

Vector Construction

Double gene vectors were constructed which contained a hEF1a promoter driving expression of both the hγ1 FL heavy chain of an anti-MUC-1 MAb and the human lambda light chain of an anti-MUC-1 MAb.

Further double gene vectors were constructed where the hEF1a promoter was exchanged for either a hCMV-MIE promoter or rat CMV promoter.

Each expression cassette within the double gene vectors consisted of the promoter functionally linked to a polynucleotide sequence encoding the CHO fibronectin signal peptide of Example 1, which was linked in frame to a polynucleotide sequence encoding the HC or LC mature polypeptide. Correct mRNA processing was ensured by the presence of a bovine growth hormone poly A sequence.

To allow selection of stable cell lines the vectors also contained a copy of the mouse dyhydrofolate reductase (dhfr) gene under control of the murine phosphoglycerate (mPGK) promoter and the hygromycin resistance gene under the control of the thymidine kinase (TK) promoter.

Routine Subculture of CHO DG44 Cells:

CHO DG44 cells were routinely cultured in suspension shaker flasks in EX-CELL ACF CHO medium (Sigma) supplemented with 8 mM L-glutamine and 1×HT supplement (Life Technologies). Cells were seeded at a concentration of $2×10^5$ cells/ml, and cells were split every 3 days. Flasks were cultured at 37° C., 7.5% $CO_2$ in an orbital shaking incubator at 140 rpm.

Transfections for Generation of Stable Cell Lines

Cells used for transfections were grown in cell suspension culture, as detailed above. Cells from growing cultures were centrifuged and re-suspended to a concentration of $2×10^7$ cells/mL. A 0.1 mL volume of the cell suspension and 4 μg of linearised plasmid DNA were added to an electroporation cuvette. The cuvette was then placed in the Amaxa nucleofector (Lonza) and nucleofected. Following transfection, the cells were added to 20 ml pre-warmed EX-CELL ACF CHO medium (Sigma) supplemented with 8 mM Glutamine and 1×HT supplement in a T75 flask. Transfected cells were incubated at 37° C., 7.5% $CO_2$. Following the removal of hypoxanthine and thymidine (HT) (48 hrs post transfection) from the medium and addition of 400 μg/ml Hygromycin B (Invitrogen) and 25 nM MTX (144 hrs post transfection) cells were plated out into 96 well plates at 5000 cells/well ($2.5×10^4$/mL). The plates were incubated at 37° C. in an atmosphere of 7.5% $CO_2$ in air. The plates were monitored for colony growth up to approximately three weeks after transfection. Supernatant from up to 100 wells containing cell growth were harvested and analysed for the Antibody using an Octet (Forte Bio) protein A assay. The top 24 expressing colonies were expanded into 24 well plates and cultured for 10 days. Supernatant was then assayed for the Antibody using an Octet (Forte Bio) protein A assay. The results are given in Table 2 below.

TABLE 2

| | hEF1α | | hCMV-MIE | | Rat CMV | |
|---|---|---|---|---|---|---|
| | 96 wp | 24 wp | 96 wp | 24 wp | 96 wp | 24 wp |
| Max Exp Level (μg/mL) | 7.3 | 18.0 | 6.1 | 3.2 | 6.1 | nd |
| Mean Exp Level (μg/mL) | 3.3 | 4.2 | 0.7 | 1.3 | 0.6 | nd |

EXAMPLE 3

Purification of Antibody from CHO Supernatant

Supernatant from recombinant CHO DG44 cell lines generated using the hEF1a promoter double gene vector described in Example 2 was purified using protein A resin. 350 mL of clarified harvest was loaded onto a pre-packed column containing MabSelect SuRe resin (GE Healthcare). Resin was washed first with 20 mM Sodium Phosphate, 1M NaCl (pH7.0) and then with 20 mM Sodium Phosphate (pH7.0). Antibody was then eluted with 100 mM Acetic acid. Recovered product was quantified using an Octet (Forte Bio) protein A assay and is shown in Table 3.

TABLE 3

| | Volume (mL) | Concentration (mg/mL) |
|---|---|---|
| Clarified Harvest | 350 | 1.3 |
| Eluted Antibody | 50.55 | 7.7 |

The invention claimed is:

1. A process of producing a target polypeptide which comprises:
   (a) expressing an expression vector for expressing a target polypeptide in a Chinese hamster ovary (CHO) host cell, the expression vector comprising an expression cassette comprising a polynucleotide encoding a recombinant polypeptide operably linked to a fibronectin secretion leader sequence comprising SEQ ID NO: 2 or a sequence having 90% sequence identity to SEQ ID NO: 2 and retaining the ability to secrete the target polypeptide; and
   (b) recovering the target polypeptide.

2. A process of producing a target polypeptide which comprises:
   (a) transfection or transformation of a Chinese hamster ovary (CHO) host cell with an expression vector for expressing a target polypeptide in a host cell, the expression vector comprising an expression cassette comprising a polynucleotide encoding the target polypeptide operably linked to a fibronectin secretion leader sequence comprising SEQ ID NO: 2 or a sequence having 90% sequence identity to SEQ ID NO: 2 and retaining the ability 10 secrete the target polypeptide;
   (b) culturing the host cell under conditions which allow proliferation of the host cell and expression and secretion of the target polypeptide from the host cell; and
   (c) recovering the target polypeptide.

3. The process according to claim 1, wherein the fibronectin secretion leader sequence corresponds to the host cell.

4. The process according to claim 1, wherein the expression cassette comprises a human elongation factor 1a (hEF1a) promoter.

5. The process according to claim 4, wherein the expression cassette comprises a polyA sequence.

6. The process according to claim 5, wherein the poly A sequence is selected from human betaglobin polyA, bovine growth hormone polyA, SV40 early and SV40 late sequences.

7. The process according to claim 1, wherein two expression cassettes are employed, a first expression cassette comprising a polynucleotide encoding a light chain of a monoclonal antibody, and a second expression cassette comprising a polynucleotide encoding a heavy chain of a monoclonal antibody.

8. The process according to claim 7, wherein the two expression cassettes comprise the same promoter, secretion leader and polyA sequence.

9. The process according to claim 8, wherein the promoter is a human elongation factor 1a (hEF1a) promoter, the fibronectin secretion leader is Chinese hamster fibronectin secretion leader and the polyA sequence is bovine betaglobin polyA sequence.

10. A process for the production of a target polypeptide, the process comprising culturing a Chinese hamster ovary cell (CHO) transfected with an expression vector comprising an expression cassette comprising a polynucleotide encoding the target polypeptide operably linked to a fibronectin secretion leader sequence comprising SEQ ID NO: 2 or a sequence having 90% sequence identity to SEQ ID NO: 2 and retaining the ability to secrete the target polypeptide.

* * * * *